United States Patent [19]

Modak et al.

[11] Patent Number: 5,985,931
[45] Date of Patent: Nov. 16, 1999

[54] TRIPLE ANTIMICROBIAL COMPOSITION

[75] Inventors: Shanta Modak, River Edge, N.J.; Lester Sampath, Nyack, N.Y.

[73] Assignee: The Trustees of Columbia University in the city of New York, New York, N.Y.

[21] Appl. No.: 09/011,841

[22] PCT Filed: Nov. 12, 1996

[86] PCT No.: PCT/US96/18104

§ 371 Date: Jun. 2, 1998

§ 102(e) Date: Jun. 2, 1998

[87] PCT Pub. No.: WO97/17849

PCT Pub. Date: May 22, 1997

[51] Int. Cl.[6] .................................................. A61K 31/155
[52] U.S. Cl. ............................................ 514/634; 514/635
[58] Field of Search ...................................... 514/634, 635

[56] References Cited

U.S. PATENT DOCUMENTS

| | | | |
|---|---|---|---|
| 3,063,895 | 11/1962 | Pearson et al. | 514/736 |
| 3,468,898 | 9/1969 | Cutler et al. | 548/211 |
| 3,506,720 | 4/1970 | Model et al. | 106/18.34 |
| 3,639,632 | 2/1972 | McNamara et al. | 514/635 |
| 3,671,644 | 6/1972 | Irani et al. | 514/114 |
| 4,022,834 | 5/1977 | Gundersen | 540/585 |
| 4,022,911 | 5/1977 | Goldhaft et al. | 514/642 |
| 4,053,636 | 10/1977 | Eustis, III et al. | 514/635 |
| 4,125,628 | 11/1978 | Goldhaft et al. | 514/642 |
| 4,134,971 | 1/1979 | Inoue et al. | 424/601 |
| 4,198,392 | 4/1980 | Juneja | 424/48 |
| 4,290,846 | 9/1981 | Muntwyler | 162/161 |
| 4,321,257 | 3/1982 | Sipos | 424/78.06 |
| 4,420,484 | 12/1983 | Gorman et al. | 514/332 |
| 4,486,405 | 12/1984 | Klein | 424/59 |
| 4,900,721 | 2/1990 | Bansemir et al. | 514/25 |
| 4,990,329 | 2/1991 | Sampathkumar | 424/53 |
| 5,017,617 | 5/1991 | Kihara et al. | 514/635 |
| 5,030,659 | 7/1991 | Bansemir et al. | 514/653 |
| 5,122,541 | 6/1992 | Eggensperger et al. | 514/578 |
| 5,244,666 | 9/1993 | Murley | 424/405 |
| 5,705,532 | 1/1998 | Modak et al. | 514/653 |

FOREIGN PATENT DOCUMENTS 9526134 of 0000 WIPO.

OTHER PUBLICATIONS

Larson and Bobo, 1992, J. Emergency Med. 10:7–11.

*Primary Examiner*—Kevin E. Weddington
*Attorney, Agent, or Firm*—Henry Y.S. Tang; Baker & Botts

[57] ABSTRACT

The present invention relates to antimicrobial compositons comprising (i) less than or equal to two percent by weight chlorhexidine or chlorhexidine salt; (ii) less than or equal to 1 percent by weight of a quaternary ammonium compound, such as benzalkonium chloride; and (iii) less than or equal to two percent by weight of parachlorometaxylenol. The antimicrobial compositions of the invention may be utilized in antimicrobial deterents, soaps, creams rinses, and emulsions for use in the medical community as well as general public use.

2 Claims, No Drawings

TRIPLE ANTIMICROBIAL COMPOSITION

1. INTRODUCTION

The present invention relates to antimicrobial compositions comprising chlorhexidine, a quaternary ammonium compound and parachlorometaxylenol. It is based, at least in part, on the discovery that chlorhexidine, benzalkonium chloride, and parachlorometaxylenol exhibit synergistic antimicrobial activity.

2. BACKGROUND OF THE INVENTION

The antimicrobial agents chlorhexidine ("CHX"; 1,6 bis ($N^5$-p-chlorophenyl-$N^1$-biguanido)hexane), benzalkonium chloride ("BZK") and parachlorometaxylenol ("PCMX") have been used, individually, in antimicrobial compositions. For example, the well-known antiseptic scrubs Hibiclens®, Ultradex® and Techni-care contain 4% CHX (Hibiclens®) and 3% PCMX (Ultradex® and Technicar®). The use of these scrubs, however, provides less than optimal antimicrobial protection, in that neither scrub is believed to be fully effective in rapidly inactivating pathogens or in reducing skin flora for an extended period of time. Furthermore, the relatively high levels of antimicrobial agents in these preparations are frequently associated with skin irritation.

Compositions which combine one or more of the foregoing antimicrobial agents with additional compounds are also known, as illustrated by the following references.

U.S. Pat. No. 5,244,666 by Murley, issued Sep. 14, 1993 ("the '666 patent") relates to an antiseptic scrub and wound disinfectant wherein a quaternary ammonium compound and a substituted phenolic compound are combined to produce enhanced antimicrobial activity at lower concentrations. The '666 patent states that the use of such combinations, together with degreasing emulsifiers, detergents, skin softeners and soothing agents is new. The compositions comprise about 3% (wt/wt) of a quaternary ammonium compound and about 3% of a substituted phenolic compound.

U.S. Pat. No. 5,030,659 by Bansemir et al., issued Jul. 9, 1991 ("the '659 patent") relates to disinfectant compositions comprising a quaternary ammonium compound, a biguanide, and a phenolic compound. The antimicrobial agent present in greatest concentration is the quaternary ammonium compound; the working examples of the '659 patent include compositions comprising 15–20% of the quaternary ammonium compound BZK.

U.S. Pat. No. 4,900,721 by Bansemir et al., issued Feb. 13, 1990, relates to liquid, aqueous disinfectants based on alcohol and hydrogen peroxide which comprise one or more $C_2$–$C_8$ alcohols, hydrogen peroxide (or a compound which produces hydrogen peroxide), one or more carboxylic acids, one or more microbicidally active nitrogen-containing organic compounds (e.g., CHX or BZK), and one or more microbicidally active phenolic compounds (including polychlorinated xylenes).

U.S. Pat. No. 4,420,484 by Gorman et al., issued Dec. 13, 1983, relates to combinations of antimicrobial agents (such as CHX or BZK) with polyethylene glycol surfactant and betaine or amine oxide surfactant.

U.S. Pat. Nos. 4,125,628 and 4,022,911, by Goldhaft et al., issued Nov. 14, 1978 and May 10, 1977, respectively, relate to combinations of a quaternary ammonium compound, a phenol or derivative thereof, and formaldehyde.

U.S. Pat. No. 3,639,632 by McNamara et al., issued Feb. 1, 1972, relates to a synergistic antimicrobial composition containing 1,1'-hexamethylenebis [5-(2-ethylhexyl) biguanide] dihydrochloride and 4-chloro-2-hydroxyphenyl, 2,4-dichlorophenyl ether.

Larson et al., 1992, J. Emergency Med. 10: 7–11 discloses that in the presence of blood, topical antimicrobial products containing alcohol were associated with greater initial reductions in colonizing flora.

The number of antimicrobial preparations which have been developed illustrates the continuing search for a composition that rapidly and effectively provides antimicrobial activity without substantial adverse effects, such as skin irritation.

3. SUMMARY OF THE INVENTION

The present invention relates to antimicrobial compositions comprising (i) less than or equal to two percent by weight chlorhexidine or chlorhexidine salt; (ii) less than or equal to 0.1 percent by weight of a quaternary ammonium compound, such as benzalkonium chloride; and (iii) less than or equal to two percent by weight of parachlorometaxylenol. The antimicrobial compositions of the invention may be utilized in antimicrobial detergents, soaps, creams, rinses, and emulsions for use in the medical community as well as general public use; they offer the advantages of effective antimicrobial activity at low concentrations of each of the active ingredients.

4. DETAILED DESCRIPTION OF THE INVENTION

The present invention relates to antimicrobial compositions comprising (i) less than or equal to two percent by weight chlorhexidine or chlorhexidine salt; (ii) less than or equal to 0.1 percent by weight of a quaternary ammonium compound, such as benzalkonium chloride; and (iii) less than or equal to two percent by weight of parachlorometaxylenol.

In a preferred, nonlimiting embodiment of the invention, where the composition is to be used as an antimicrobial scrub, the concentration of chlorhexidine or chlorhexidine salt is between one and two percent (inclusive). In alternate nonlimiting embodiments of the invention, the concentrations of chlorhexidine or chlorhexidine salt in the compositions are between 0.05 and 0.1 percent by weight (inclusive), and, in specific embodiments, equal to 0.05 percent or 0.1 percent by weight. The term "chlorhexidine" refers to non-salt compositions of chlorhexidine, including chlorhexidine free base. Chlorhexidine salts that may be used according to the invention include but are not limited to the following: chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate.

Compositions may alternatively comprise less than 2 percent (preferably 0.025–0.1%) polyhexamethylene biguanide ("PHMB").

Quaternary ammonium compounds that may be used according to the invention include, but are not limited to, benzalkonium chloride (BZK), benzethonium chloride, other benzalkonium or benzethonium halides, cetylpyridinium chloride, dequalinium chloride, N-myristyl-N-methylmorpholinium methyl sulfate, poly[N-[3-(dimethylammonio)propyl]-N'-[3-(ethyleneoxyethelene dimethylammonio)propyl]urea dichloride], alpha-4-[1- tris (2-hydroxyethyl)ammonium chloride-2-butenyl]-omega-tris (2-hydroxyethyl)ammonium chloride, alpha-4-[1-tris(2-hydroxyethyl)ammonium chloride-2-butenyl]poly[1-dimethyl ammonium chloride-2-butenyl]-omega-tris(2-hydroxyethyl)ammonium chloride, poly [oxy-ethylene (dimethyliminio)ethylene (dimethyliminio)-ethylene dichloride], ethyl hexadecyl dimethyl ammonium ethyl sulfate, dimethyl ammonium ethyl sulfate, dimethylethylbenzyl ammonium chloride, dimethylbenzyl ammonium chloride, and cetyldimethylethyl ammonium bromide. In preferred nonlimiting embodiments, the quaternary ammonium compound is benzalkonium chloride.

In particularly preferred nonlimiting embodiments of the invention, where the composition is to be used as an antimicrobial scrub, the concentration of benzalkonium chloride is less than or equal to 0.1 percent. In alternate embodiments, the concentration of benzalkonium chloride is between 0.005 and 0.01 percent by weight (inclusive).

The compositions of the invention may further comprise an organic solvent that aids in the dissolution of the antimicrobial agents, for example, isopropanol or propylene glycol. The amount of isopropanol in the compositions of the invention is preferably between 2.5 and 5 percent by weight (inclusive). In specific preferred embodiments, the amount of isopropanol is 5 percent by weight.

In preferred embodiments of the invention, where the composition is to be used as an antimicrobial scrub, the amount of parachlorometaxylenol is less than or equal to 2 percent. In alternate embodiments, the amount of parachlorometaxylenol is between 0.05 and 0.25 percent by weight, inclusive.

In yet another embodiment, the present invention provides for a scrub base that is believed to enhance the effectiveness of antimicrobial agents. This base comprises 10–15 percent of a pluronic copolymer surfactant, including but not limited to pluronic F87; 1–5 percent of an amine oxide foaming agent, including but not limited to lauryl dimethylamine oxide; 0.2–0.25 percent of a foam enhancer such as, but not limited to, glucamate DOE 120; one or more antimicrobial agent; and water, wherein the pH has been adjusted to 5.5–6.0 with a mild acid such as, but not limited to, gluconolactone, lactic acid, salicylic acid, citric acid or gluconic acid. Suitable antimicrobial agents include, but are not limited to, parachlorometaxylenol, phenoxyethanol, povidone iodine, chlorhexidine or a chlorhexidine salt, benzalkonium chloride, and combinations thereof. Compounds such as isopropanol or propylene glycol may also be used to improve the solubility of antimicrobial agent.

It has surprisingly been found that, contrary to the teachings of the prior art, a non-ionic surfactant such as Pluronic F87 is compatible with parachlorometaxylenol. The prior art generally teaches the use of amphoteric or anionic surfactants in parachlorometaxylenol formulations.

The compositions of the invention may be incorporated into a variety of products, including, but not limited to hand disinfectants, hand soaps, topical creams, antiseptic rinses or soaks, and antiseptic towlettes. Likewise, they may be incorporated as preservatives, for example, in cosmetics.

Such products may be prepared according to methods known in the art. The present invention provides for the following specific, preferred, nonlimiting embodiments:

The present invention provides for an antimicrobial scrub having the following composition: 2 grams parachlorometaxylenol; 2 grams chlorhexidine digluconate; 0.1 gram benzalkonium chloride; 5.0 ml isopropanol; 12.5 grams pluronic F87; 1.8 grams lauryl dimethylamine oxide; 0.25 grams glucamate DOE; 1 gram D-glucanolactone; and 75.35 grams deionized water; wherein the pH is adjusted to between 5.5–6.0 with D-glucanolactone. In related embodiments, 2–10 percent cocamidopropyl betaine may be added to the above-identified composition.

In another related embodiment, the present invention provides for an antimicrobial scrub having the following composition: 2 grams parachlorometaxylenol; 2 grams chlorhexidine digluconate; 0.1 gram benzalkonium chloride; 10 grams propylene glycol; 12.5 grams pluronic F87; 1.8 grams lauryl dimethylamine oxide; 0.25 grams glucamate DOE; 1 gram D-glucanolactone; and 75.35 grams deionized water; wherein the pH is adjusted to between 5.5–6.0 with D-glucanolactone. In related embodiments, 2–10 percent cocamidopropyl betaine may be added to the above-identified composition.

In another specific embodiment, the present invention provides for an antimicrobial scrub having the following composition: 3 percent parachlorometaxylenol; 1 percent phenoxyethanol; 10 percent propylene glycol; 10 percent pluronic F87; 1.8 percent lauryl dimethylamine oxide; 0.25 percent glucamate DOE 120; 1 percent D-gluconolactone; and 73 percent deionized water. In a related embodiment, this scrub may further comprise 0.1 percent benzalkonium chloride. In still further related embodiments, such a scrub, with or without benzalkonium chloride, may further comprise 2–10 percent cocamidopropyl betaine.

In another specific embodiment, the present invention provides for an antimicrobial scrub having the following composition: 5 percent povidone iodine; 10 percent propylene glycol; 1 percent phenoxyethanol; 10 percent pluronic F87; 1.8 percent lauryl dimethamine oxide; 0.25 percent glucamate DOE 120; 1 percent D-gluconolactone; and 71 percent deionized water.

In yet another specific embodiment, the present invention provides for an antimicrobial scrub having the following composition: 5 percent povidone iodine; 10 percent propylene glycol; 10 percent Pluronic F87; 1.8 percent lauryl dimethylamine oxide; 0.25 percent glucamate DOE; 1 percent D-gluconolactone; and 72 percent deionized water.

In another specific embodiment, the present invention provides for an antimicrobial scrub having the following composition: 3 percent parachlorometaxylenol; 10 percent propylene glycol; 1 percent phenoxyethanol; 10 percent pluronic F87; 1.8 percent lauryl dimethamine oxide; 0.25 percent glucamate DOE 120; 1 percent D-gluconolactone; and 71 percent deionized water.

In yet another specific embodiment, the present invention provides for an antimicrobial scrub having the following composition: 3 percent parachlorometaxylenol; 10 percent propylene glycol; 10 percent Pluronic F87; 1.8 percent lauryl dimethylamine oxide; 0.25 percent glucamate DOE; 1 percent D-gluconolactone; and 72 percent deionized water.

The compositions of the invention may further comprise quaternaries such as isostearyl ethylimidonium ethosulfate ("ISIES"), polyoxyethylene dihydroxypropyl linoleaminium chloride ("SL-5"), and bishydroxyethyl dihydroxypropyl stearaminium chloride ("TG"), and phospholipids such as cocamidopropyl phosphatidyl PG-dimonium chloride ("PTC"), linoleamidopropyl phosphatidyl PG-dimonium chloride ("EFA"), and stearamidopropyl phosphatidyl PG-dimonium chloride and cetyl alcohol ("SV"), obtainable from Mona Industries, Paterson, N.J.

The usefulness of the present invention is demonstrated by the following examples, set forth as examples only, and not by way of limitation. It should be noted that the concentrations of active agents are lower than those used in currently available products, thereby diminishing the risk of skin irritation, but providing effective antimicrobial protection.

5. EXAMPLES: SYNERGISM OF PCMX, CHX AND BZK

Table 1 shows the results when various concentrations of PCMX in 2.5% isopropanol ("ISOPR") were exposed to *Staphylococcus aureus* bacteria. To produce each sample, 0.1 ml of a ten-fold concentrated antimicrobial solution was added to 0.9 ml of TSB broth containing 20% serum and $10_7$ colony forming units (CFU) of *Staphylococcus aureus*. After one minute, a 50 microliter aliquot from each sample was diluted to a volume of 10 ml with LTSB drug inactivating medium (5% Tween 80, 2% lecithin, 0.6% sodium oleate, 0.5% sodium thiosulfate, 0.1% protease peptone and 0.1% tryptone), and then 0.5 ml of the diluted culture was plated on trypticase soy agar plates. The plates were incubated at 37° C. for 24 hours, and then colony counts per milliliter of the original 1 ml antimicrobial containing culture were determined.

TABLE 1

| Sample | A1 | B1 | C1 | D1 | E1 | F1 |
|---|---|---|---|---|---|---|
| %PCMX | 0 | .01 | .02 | .03 | .04 | .05 |
| %ISOPR | 2.5 | 2.5 | 2.5 | 2.5 | 2.5 | 2.5 |
| CFU/ml | $1 \times 10^7$ | $8 \times 10^6$ | $4 \times 10^6$ | $3.5 \times 10^6$ | $1.8 \times 10^5$ | $1 \times 10^6$ |

Table 1 demonstrates that as the concentration of PCMX was increased from 0 to 0.05%, a reduction of CPU by approximately a factor of ten was observed.

Table 2 shows the results of experiments in which 0.05% chlorhexidine was added to the compositions tested in Samples A1–F1, as described in Table 1. The corresponding samples, containing 0.05% chlorhexidine, are designated A2–F2.

TABLE 2

| Sample | A2 | B2 | C2 | D2 | E2 | F2 |
|---|---|---|---|---|---|---|
| %PCMX | 0 | .01 | .02 | .03 | .04 | .05 |
| %CHX | .05 | .05 | .05 | .05 | .05 | .05 |
| %ISOPR | 2.5 | 2.5 | 2.5 | 2.5 | 2.5 | 2.5 |
| CFU/ml | $8 \times 10^6$ | $2 \times 10^5$ | $7 \times 10^4$ | $7 \times 10^3$ | 0 | 0 |

Table 2 demonstrates that 0.05% CHX, used alone, had very little effect on the number of CFU present in control sample A1 ($1 \times 10^7$ CFU), in that control sample A2 exhibited $8 \times 10^6$ CFU. Similarly, sample B1, which contained 0.01% PCMX, exhibited $8 \times 10^6$ CFU. However, the combination of 0.01% PCMX and 0.05% CHX in sample B2 resulted in an approximately 40- fold drop in the number of CFU relative to control A2 (to $2 \times 10^5$ CFU). Moreover, although 0.03% PCMX reduced the number of CFU by a factor of 3 relative to control A1 to $3.5 \times 10^6$ (sample D1), the combination of 0.03% PCMX and 0.05% CHX decreased the number of CFU by approximately a factor of 1000 relative to control A2 (to $7 \times 10^3$ CFU, sample D2). The combination of 0.04% PCMX and 0.05% CHX eliminated all CFU (sample E2). This data demonstrates the synergistic antimicrobial activity of PCMX and CHX, and is corroborated by data presented in Table 3, which combines the amount of PCMX contained in samples A1–F1 with 0.1% CHX, in corresponding samples A3–F3.

TABLE 3

| Sample | A3 | B3 | C3 | D3 | E3 | F3 |
|---|---|---|---|---|---|---|
| %PCMX | 0 | .01 | .02 | .03 | .04 | .05 |
| %CHX | .1 | .1 | .1 | .1 | .1 | .1 |
| %ISOPR | 2.5 | 2.5 | 2.5 | 2.5 | 2.5 | 2.5 |
| CFU/ml | $9 \times 10^5$ | $7 \times 10^4$ | $4 \times 10^4$ | $1.2 \times 10^3$ | 0 | 0 |

Experiments have also demonstrated the synergistic activity of BZK with PCMX and CHX. Table 4 shows the results of experiments in which 0.01% BZK was added to the compositions of samples A1 and B2–F2, thereby testing 0.01% BZK used alone or in combination with 0.05% CHX and 0.01–0.05% PCMX in samples A4–F4. Of note, a control sample for the samples set forth in Table 4, which contained 2.5% ISOPR and no antimicrobial, exhibited $1.2 \times 10^7$ CFU (not set forth in Table 4).

TABLE 4

| Sample | A4 | B4 | C4 | D4 | E4 | F4 |
|---|---|---|---|---|---|---|
| %PCMX | 0 | .01 | .02 | .03 | .04 | .05 |
| %CHX | 0 | .05 | .05 | .05 | .05 | .05 |
| %BZK | .01 | .01 | .01 | .01 | .01 | .01 |
| %ISOPR | 2.5 | 2.5 | 2.5 | 2.5 | 2.5 | 2.5 |
| CFU/ml | $4 \times 10^6$ | $8 \times 10^2$ | 0 | 0 | 0 | 0 |

Table 4 shows that despite the fact that 0.01% BZK alone (sample A4; $4 \times 10^6$ CFU) decreased the number of CFU by a factor of only 3 relative to the control sample ($1.2 \times 10^7$ CFU), and sample B2 (0.01% PCMX+0.05% CHX) decreased the number of CFU by a factor of approximately 40 relative to control A2, sample B4 (0.01% PCMX+0.05% CHX+0.01% BZK) exhibited an approximately 10,000-fold decrease in the number of CFU relative to control A4. This data demonstrates the synergistic antimicrobial activity of low concentrations of PCMX, CHX, and BZK, and is corroborated by the data presented in Table 5, which combines the same amounts of PCMX and CHX with 0.005% BZK in samples A5–F5.

TABLE 5

| Sample | A5 | B5 | C5 | D5 | E5 | F5 |
|---|---|---|---|---|---|---|
| %PCMX | 0 | .01 | .02 | .03 | .04 | .05 |
| %CHX | 0 | .05 | .05 | .05 | .05 | .05 |
| %BZK | .005 | .005 | .005 | .005 | .005 | .005 |
| %ISOPR | 2.5 | 2.5 | 2.5 | 2.5 | 2.5 | 2.5 |
| CFU/ml | $5 \times 10^6$ | $1.2 \times 10^3$ | 0 | 0 | 0 | 0 |

The experiments described in Tables 1–5 were then repeated, except that the amount of isopropanol was increased to 5%

Table 6 depicts the results of experiments in which the amount of isopropanol in samples A1–F1 (Table 1) were increased to 5%.

TABLE 6

| Sample | A6 | B6 | C6 | D6 | E6 | F6 |
|---|---|---|---|---|---|---|
| %PCMX | 0 | .01 | .02 | .03 | .04 | .05 |
| %ISOPR | 5 | 5 | 5 | 5 | 5 | 5 |
| CFU/ml | $1 \times 10^7$ | $4 \times 10^6$ | $2 \times 10^6$ | $1.5 \times 10^6$ | $9 \times 10^5$ | $8 \times 10^5$ |

The number of CFU in samples A6–F6 were substantially the same (perhaps slightly less) than those exhibited by samples A1–F1.

Table 7 depicts the results of experiments in which the amount of isopropanol in samples, which otherwise correspond to samples A2–F2 (Table 2), was increased to 5%.

TABLE 7

| Sample | A7 | B7 | C7 | D7 | E7 | F7 |
|---|---|---|---|---|---|---|
| %PCMX | 0 | .01 | .02 | .03 | .04 | .05 |
| %CHX | .05 | .05 | .05 | .05 | .05 | .05 |
| %ISOPR | 5 | 5 | 5 | 5 | 5 | 5 |
| CFU/ml | $1 \times 10^6$ | $1.5 \times 10^5$ | $3.5 \times 10^4$ | $1.6 \times 10^3$ | 0 | 0 |

The data presented in Table 7 again demonstrates the synergistic relationship between CHX and PCMX. Further, the increase in the concentration of ISOPR from 2.5 to 5% seems to have slightly decreased the number of CFU. These results are further corroborated by data presented in Table 8, which relates to samples essentially the same as samples A3–F3 (Table 3), except that the amount of isopropanol was increased from 2.5 to 5%.

TABLE 8

| Sample | A8 | B8 | C8 | D8 | E8 | F8 |
|---|---|---|---|---|---|---|
| %PCMX | 0 | .01 | .02 | .03 | .04 | .05 |
| %CHX | .1 | .1 | .1 | .1 | .1 | .1 |
| %ISOPR | 5 | 5 | 5 | 5 | 5 | 5 |
| CFU/ml | $9 \times 10^5$ | $4.5 \times 10^4$ | $1.5 \times 10^3$ | 0 | 0 | 0 |

Table 9 presents the results of experiments in which the amount of isopropanol, in samples corresponding to samples A4–F4 (Table 4), was increased from 2.5% to 5%. A control sample for the samples set forth in Table 9, containing 5% ISOPR and no antimicrobial exhibited $1.2 \times 10^7$ CFU (not shown in Table 9).

TABLE 9

| Sample | A9 | B9 | C9 | D9 | E9 | F9 |
|---|---|---|---|---|---|---|
| %PCMX | 0 | .01 | .02 | .03 | .04 | .05 |
| %CHX | 0 | .05 | .05 | .05 | .05 | .05 |
| %BZK | .01 | .01 | .01 | .01 | .01 | .01 |
| %ISOPR | 5 | 5 | 5 | 5 | 5 | 5 |
| CFU/ml | $1.5 \times 10^6$ | $2.6 \times 10^2$ | 0 | 0 | 0 | 0 |

This data corroborates the synergistic relationship between CHX, PCMX, and BZK and further shows that an increase in the amount of isopropanol to 5% decreased CFU slightly. This conclusion is further supported by the results depicted in Table 10, where samples otherwise corresponding to samples A5–F5 (Table 5) contained 5%, rather than 2.5%, isopropanol.

TABLE 10

| Sample | A10 | B10 | C10 | D10 | E10 | F10 |
|---|---|---|---|---|---|---|
| %PCMX | 0 | .01 | .02 | .03 | .04 | .05 |
| %CHX | 0 | .05 | .05 | .05 | .05 | .05 |
| %BZK | .005 | .005 | .005 | .005 | .005 | .005 |
| %ISOPR | 5 | 5 | 5 | 5 | 5 | 5 |
| CFU/ml | $1.5 \times 10^6$ | $1.2 \times 10^3$ | 0 | 0 | 0 | 0 |

The synergistic effectiveness of low concentrations of CHX and PCMX (in 5% isopropanol) in the presence of blood was also demonstrated, as shown in Table 11.

TABLE 11

| Antimicrobial | CFU/ml |
|---|---|
| None (control) | $3 \times 10^6$ |
| .5% CHX | $1 \times 10^5$ |
| 1% CHX | $1 \times 10^4$ |
| .125% PCMX | $1 \times 10^6$ |
| .25% PCMX | $1.4 \times 10^4$ |
| .5% PCMX | 0 |
| .5% CHX + .25% PCMX | 0 |
| 1% CHX + .125% PCMX | 0 |

6. EXAMPLE: COMPARISON OF SCRUBS PREPARED ACCORDING TO THE INVENTION

The following antimicrobial scrubs were tested for antimicrobial effectiveness.

Scrub A. 3% PCMX
    1% phenoxyethanol
    10% propylene glycol
    10% pluronic F87
    1.8% lauryl dimethylamine oxide
    0.25% glucamate DOE 120
    1% D-gluconolactone
    73% deionized water Scrub B. Scrub A+0.1% BZK Scrub C. 3% PCMX
    5% isopropanol
    12.5% pluronic F87
    1.8% lauryl dimethylamine oxide
    0.25% glucamate DOE 120
    1.0% D-glucanolactone
    76.45% deionized water To assess antimicrobial effectiveness, 0.1 ml of each scrub was mixed with 0.9 ml of a culture of *Staphylococcus aureus* in TSB containing 10% serum, at $10^6$ CFU per ml. After 15 seconds, a 50 microliter aliquot was removed and diluted to 10 ml using drug inactivating medium (LTSB, see above), and 0.5 ml of the diluted culture was plated onto trypticase soy agar. After incubation at 37° C. for 24 hours, colony counts were determined, and the results are shown in Table 12.

TABLE 12

| Scrub | CFU/ml |
|---|---|
| A | 0 |
| B | 0 |
| C | $6 \times 10^3$ |
| Hibiclens | $3 \times 10^4$ |
| Technicare | $6 \times 10^5$ |
| Ultradex | $1 \times 10^5$ |

7. EXAMPLE: ENHANCED ACTIVITY IN NEW SCRUB BASE

Various antimicrobial agents and compositions were combined in the following base (made to a volume of 100 ml with deionized water):

5% isopropanol 12.5% pluronic F87

1.8% lauryl dimethylamine oxide 0.25% glucamate DOE 120

1.0% D-glucanolactone

These compositions were tested for antimicrobial effectiveness using the same method set forth in Section 6, above. The results are shown in Table 13. The scrub base appeared to enhance the effectiveness of PCMX in particular.

TABLE 13

| Scrub Base + antimicrobial | CFU/ml |
| --- | --- |
| 2% chlorhexidine digluconate + 2% PCMX + 0.1% BZK | 0 |
| 2% PCMX | $1.2 \times 10^4$ |
| 3% PCMX | $6.0 \times 10^3$ |
| 2% chlorhexidine digluconate | $7.0 \times 10^4$ |
| 4% chlorhexidine digluconate | $1.0 \times 10^4$ |
| 0.1% BZK | $1.5 \times 10^6$ |
| 3% PCMX + 0.1% BZK | $5.0 \times 10^2$ |
| Hibiclens | $3.0 \times 10^4$ |
| Technicare | $6.0 \times 10^5$ |
| Ultradex | $1 \times 10^5$ |
| Control | $7.0 \times 10^6$ |

8. EXAMPLE: NEW SCRUB BASE WITH PROPYLENE GLYCOL

Using the same methodology for antimicrobial testing set forth above, the effectiveness of the following scrub was tested, and compared to a commercially available scrub containing povidone iodine (Betadine®, which contains 10 percent povidone iodine).

Scrub D:

5% povidone iodine

10% propylene glycol

1% phenoxyethanol

10% Pluronic F87

1.8% lauryl dimethylamine oxide 0.25% glucamate DOE 120

1% D-gluconolactone

71% deionized water

TABLE 14

| Scrub | CFU/ml |
| --- | --- |
| Scrub D | 0 |
| Betadine | $3.0 \times 10^2$ |
| Control | $1.7 \times 10^6$ |

9. EXAMPLE: SCRUB COMPRISING POLYHEXAMETHYLENE BIGUANIDE

Using the same methods set forth in example section 5, above, the rate of kill of compositions comprising PHMB, PCMX, BZK and PXE were tested. As demonstrated by Table 15, synergy was observed between BZK, PHMB, and PCMX at respective concentrations of 0.01%, 0.05%, and 0.05%. Synergy was also observed among 0.1% PXE+ 0.05% PHMB+0.05% PCMX.

TABLE 15

Rate of Kill of Polyhexamethylene (PHMB), Parachlorometaxylenol (PCMX), Benzalkonium Chloride (BZK), and Phenoxyethanol (PXE) Singly and in Combination vs Staphyclococcus aureus.

| ANTIMICROBIALS | CONCENTRATION % | CFU/mL |
| --- | --- | --- |
| PHMB | 0.1 | $4.0 \times 10^6$ |
| PHMB | 0.05 | $2.0 \times 10^6$ |
| PHMB | 0.025 | $5.0 \times 10^6$ |
| PCMX | 0.1 | $1.6 \times 10^3$ |
| PCMX | 0.05 | $5.0 \times 10^6$ |
| PXE | 0.1 | $2.0 \times 10^7$ |
| BZK | 0.02 | $2.0 \times 10^7$ |
| PHMB + PCMX | 0.05 + 0.05 | $2.6 \times 10^4$ |
| PHMB + PCMX | 0.025 + 0.025 | $6.0 \times 10^5$ |
| PHMB + PCMX + BZK | 0.05 + 0.05 + 0.1 | $2.2 \times 10^3$ |
| PHMB + PCMX + PXE | 0.05 + 0.05 + 0.1 | $1.9 \times 10^3$ |
| PHMB + PCMX + PXE | 0.025 + 0.025 + 0.1 | $1.1 \times 10^5$ |
| Control | none | $2.0 \times 10^7$ |

Various publications are cited herein, the disclosures of which are hereby incorporated by reference in their entireties.

We claim:

1. An antimicrobial composition comprising
   (i) greater than zero and less than or equal to two percent of polyhexamethylene biguanide;
   (ii) greater than zero and less than or equal to 0.1 percent of a quaternary ammonium compound; and
   (iii) greater than zero and less than or equal to two percent parachlorometaxylenol; wherein the combination of (i), (ii) and (iii) exhibits effective antimicrobial activity.
2. The composition of claim 1 wherein the amount of polyhexamethylene biguanide is about 0.025–0.1 percent.

* * * * *